United States Patent [19]
Sallberg et al.

[11] Patent Number: 4,802,365
[45] Date of Patent: Feb. 7, 1989

[54] MULTI-AXIAL FATIGUE TESTING MACHINE

[75] Inventors: David W. Sallberg; Timothy J. Lawson, both of Farmington Hills; Maurice H. Cardon, Rochester, all of Mich.

[73] Assignee: Schenck Pegasus Corporation, Troy, Mich.

[21] Appl. No.: 158,605

[22] Filed: Feb. 22, 1988

[51] Int. Cl.⁴ ............................................. G01N 3/32
[52] U.S. Cl. ........................................ 73/808; 73/816
[58] Field of Search ................... 73/794–798, 73/806, 808, 810, 812–816, 865.9, 865.3

[56] References Cited

U.S. PATENT DOCUMENTS

| | | | |
|---|---|---|---|
| 1,379,961 | 5/1921 | Chilton | 73/865.9 |
| 3,277,701 | 10/1966 | Tannenberg | 73/794 |
| 3,304,768 | 2/1967 | Naumann et al. | 73/794 |
| 3,381,526 | 5/1968 | Rastogi et al. | 73/810 |
| 3,580,059 | 5/1971 | Dalton | 73/865.9 |
| 3,712,125 | 1/1973 | Meyer | 73/816 |
| 3,719,346 | 3/1973 | Bohannon et al. | 73/865.9 |
| 4,089,211 | 5/1978 | Vercellone et al. | 73/797 |
| 4,658,656 | 4/1987 | Haeg | 73/798 |
| 4,718,281 | 1/1988 | Crews, Jr. | 73/794 |

FOREIGN PATENT DOCUMENTS 0877405 10/1981 U.S.S.R. .................. 73/865.9

Primary Examiner—Stewart J. Levy
Assistant Examiner—Robert R. Raevis
Attorney, Agent, or Firm—Reising, Ethington, Barnard, Perry & Milton

[57] ABSTRACT

A machine for testing ball joints, elastomer bushings or other parts has a pair of mutually rotated gimbals attached to the outer shell or element for applying rotational displacements about two axes and a linear input attached to the inner element to apply a force along another axis. Each axis input is effected by a linear actuator and the gimbal inputs are specially designed to assure accurate independent control without parasitic motion between the inputs. Force and displacement transducers monitor each axis to provide feedback signals to control circuits. A heat chamber including the gimbal assembly has hot air applied from an external source through a hollow gimbal hub to hold the test specimen at a desired temperature.

9 Claims, 4 Drawing Sheets

MULTI-AXIAL FATIGUE TESTING MACHINE

FIELD OF THE INVENTION

This invention relates to a testing machine and particularly to such a machine for multi-axial fatigue testing of components having inner and outer elements subject to a linear load as well as to torques applied about different axes such as ball joints, elastomer bushings and the like.

BACKGROUND OF THE INVENTION

It is desirable to test bushings of the kind, for example, used in automotive vehicle suspensions for the purpose of quality control and, if possible, for testing during the process of developing a bushing or even during the development of the suspension system using the bushing.

The manner of fatigue failure of elastomers is an extremely complex phenomenon which is very difficult to predict due to the combination of physical and chemical deterioration. Several important factors affecting fatigue life are cyclic strain, prestress, environment, geometry, and composition. Failure begins when the material is unable to support local deformations. Flex cracks occur at points surrounding surface imperfections or filler boundaries, and grow upon repeated flexing.

In bushing testing, relatively large deflections place a demand on the test machine to physically constrain the test part in a manner closely approximating the actual end use. Improper constraint may drastically effect the performance of the specimen.

One approach to bushing testing is to test the sample using the entire end use assembly and real time loading conditions. This, however, presupposes the existence of a completed assembly and its availability for bushing test purposes. Road tests on an actual vehicle, if one exists with an appropriate suspension, are very useful but require that the vehicle be instrumented for the test and that a suitable road surface be available for the desired test.

The parallel development of the bushing and suspension often afford certain economic advantages. For this purpose the testing machine must be very flexible in terms of the kinds of input forces that can be applied and how well they can be controlled to simulate the forces arising from particular road surfaces and suspension designs.

The analysis of test results including statistical analysis is important in determining the physical properties of the specimen under test and to recognize the failure mode which may be defined as a change in spring rate, reduction in ultimate strength or complete sample failure, for example.

Testing machines for ball joints and the like with similar objectives have been proposed. In such machines inner and outer gimbals are rocked about their respective axes to afford the necessary imposition of torques on the test specimen. The outer gimbal carries the inner gimbal and also carries an actuator for driving the inner gimbal. The mass of the actuator causes the outer gimbal to be very much out of balance and increases the inertia of the outer gimbal so that its oscillation is limited to a frequency of about one Hertz, which is too low for many tests. In addition, hydraulic hoses attached to the actuator must withstand the constant flexing imposed by the oscillatory motion of the outer gimbal.

In addition to obviating the above problems with prior devices it is desirable to provide the ability to monitor rotary amplitudes of motion and load within 1% of their programmed amplitude. Since elastomers are temperature sensitive, it is also important to control the ambient temperature between 50° and 120 degrees C. There is a conflict between the monitoring requirements and the temperature requirements since transducers should be coupled directly to the axis of motion to obtain the desired accuracy, but standard transducers which are economical to use generally do not operate in the required temperature range.

SUMMARY OF THE INVENTION

It is therefore an object of the invention to provide a testing machine for bushings, ball joints and the like operable at higher frequencies of oscillation. It is a further object to provide a specimen heating environment for such a testing machine which does not effect the transducers monitoring the load and motion.

The invention is carried out by a testing machine for multi-axis fatigue testing of a component having an outer element and an inner element subject to linear and torsional stresses comprising a base, first, second a third hydraulic actuators secured to the base, hydraulic pressure means and control means coupled to the actuators for controlled operation of the actuators, gimbal means comprising first and second gimbals mounted on the base and interconnected for rotation about mutually perpendicular axes, the first gimbal having means for attachment to one of the elements, means for independently coupling the first and second actuators to the first and second gimbals respectively so that each actuator effects rocking movement of one gimbal without inputting torque about the axis of the other gimbal, and means for attaching the third actuator to the other of the elements whereby the three actuators independently and controllably apply loads to the bushing about three axes of motion.

The invention further comprehends defining a test chamber by the gimbals and supplying heated air to the chamber for heating the specimen. It is a further feature that one of the gimbals has a tubular pivot member providing a passage for heating air from an external source to the chamber.

BRIEF DESCRIPTION OF THE DRAWINGS

The above and other advantages of the invention will become more apparent from the following description taken in conjunction with the accompanying drawings wherein like references refer to like part and wherein.

DESCRIPTION OF THE PREFERRED EMBODIMENT

The invention in its preferred form is directed to a testing machine for bushings of the type comprising a hollow cylindrical elastomer bounded by inner and outer steel sleeves. It will, however, be apparent that parts other than bushings can be tested on this machine. For example ball joints or other components with inner and outer elements subject to linear and rotational forces or displacements about different axes can also be tested.

The testing machine as applied to bushings has a fixture which separately clamps the inner and outer sleeves and three independently controlled actuators apply forces to the sleeves on three axes of motion. Linear motion is applied along one axis and rotary or oscillating motion is applied about two mutually perpendicular axes. The motion or forces are applied in a controlled manner according to the design of the particular test until the elastomer fails as evidenced by touching of the inner and outer sleeves. During the test the bushing is held at a controlled elevated temperature. The description will begin with an explanation of the overall system, particularly the controls, and then the fixture will be described.

Figure 1:
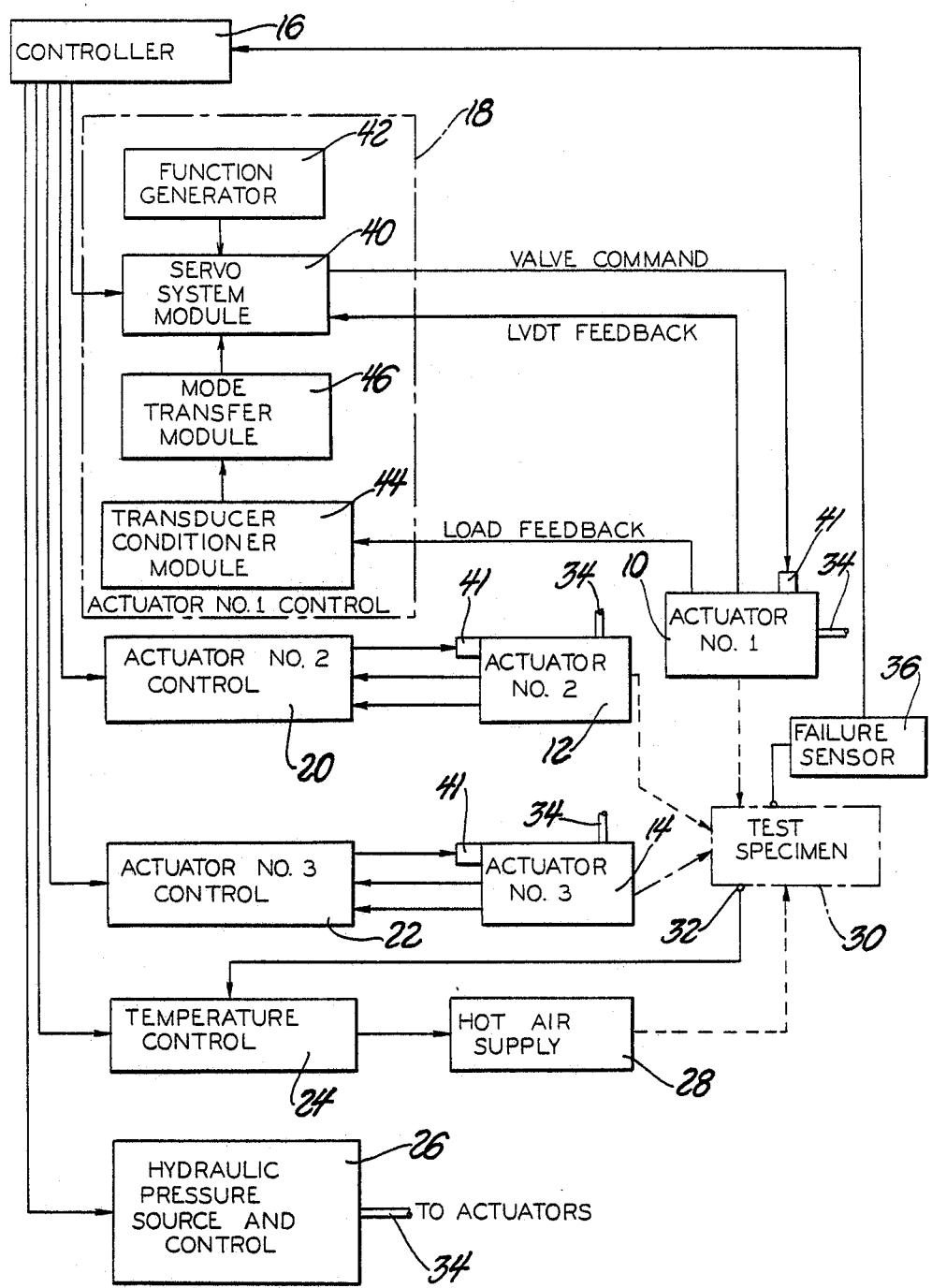
FIG. 1 is a block diagram of the test control system for the testing machine of the invention.

The test control system of FIG. 1 comprises an array of commercially available electronic modules dedicated to the operation of actuators 10, 12 and 14, and control of the hydraulic pressure for the actuators and of the test temperature. A programmable controller 16 has supervisory control over the system and is coupled to each of three specific actuator controls 18, 20 and 22 which determine the operation of the actuators 10, 12 and 14 respectively. A temperature control 24 and a pressure control 26 are also connected to the controller 16. The temperature control 24 regulates the output of a hot air supply 28 which heats the test specimen 30. A thermocouple 32 on or near the test specimen 30 supplies a temperature feedback to the temperature control 24. The hydraulic pressure source and control 26 provides pressure on the order of 3000 psi to the actuators via line 34. A failure sensor 36 coupled to the specimen 30 provides a failure feedback signal to the controller 16.

The actuator controls 18, 20 and 22 are substantially alike so that a description of actuator control 18 will suffice for all. A servo system module 40 under control of the controller 16 comprises a servo amplifier for outputting a valve command to a servovalve 41 on the actuator 10 as well as electronics for excitation and signal conditioning for an actuator position transducer. The transducer comprises a linear variable differential transformer (LVDT) packaged in the actuator for accurate monitoring of the actuator position and the LVDT feedback is coupled to the servo system module. Alternatively, a rotary variable differential transducer (RVDT) mounted externally of the actuator on a rotatable element can be used to provide direct information on the rotary position of an input to the specimen. A function generator 42 provides the driving signal waveform for the actuator 10. Any desired motion can be programmed into the generator 42 to obtain, for example, sinusoidal signals or random signals, or recorded road data can be used to generate drive signals. The drive signals from the actuator control 18 can be wholly independent of the drive signals from the controls 20 and 22 or they may all be coordinated in a desired phase relationship. This arrangement provides a position control loop. A load feedback loop is also provided.

To afford a load control loop a load cell associated with the actuator 10 provides a feedback signal to a transducer conditioner module 44 in the controller 18. The module 44 provides excitation and signal conditioning for the load cell. A mode transfer module 46 coupled between the transducer conditioner module 44 and the servo system module 40 provides the capability to switch between position and load control modes without adjusting gains or the risk of losing control of the actuator.

Figure 2:
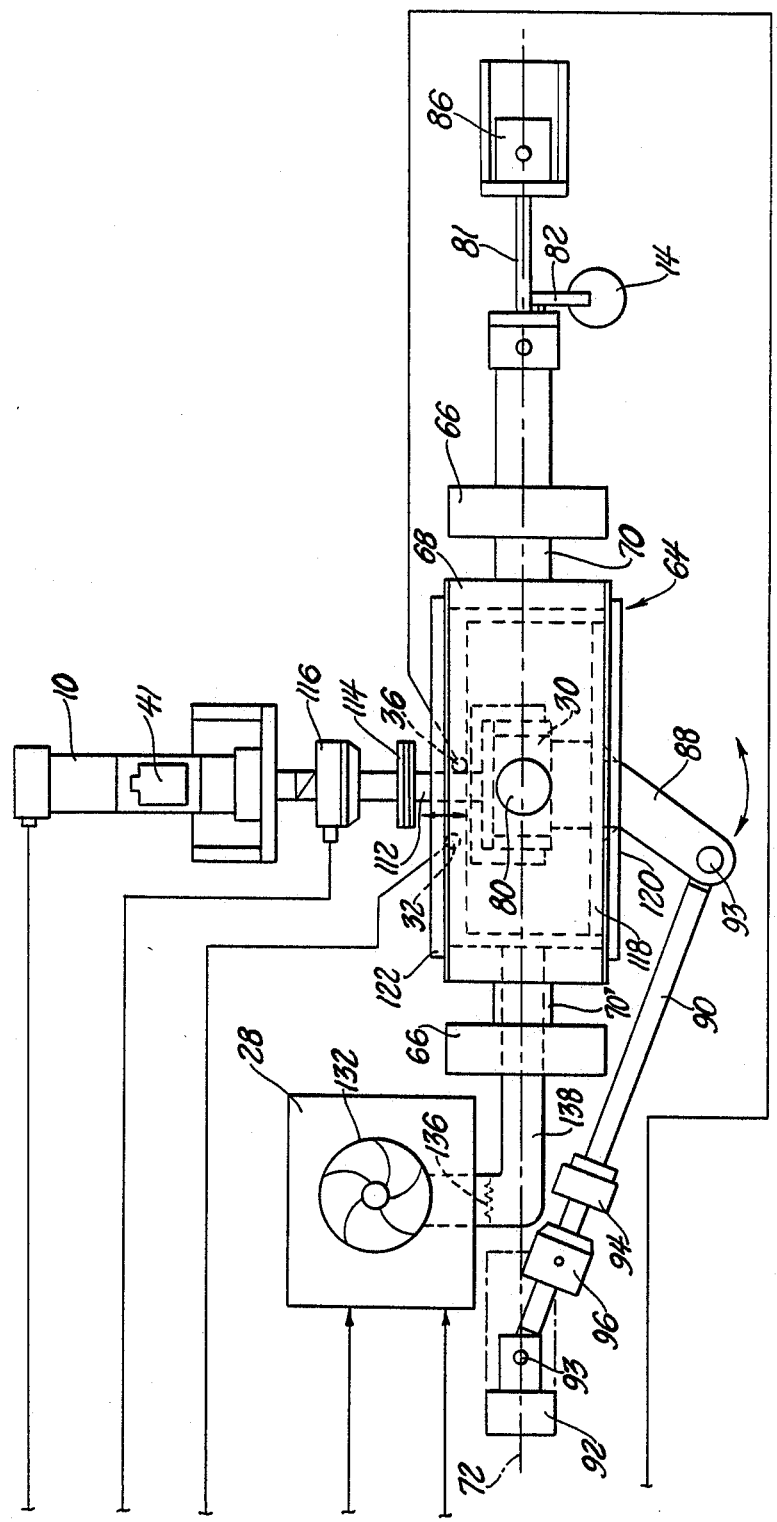
FIG. 2 is a schematic top view of the testing machine according to the invention.
Figure 3:
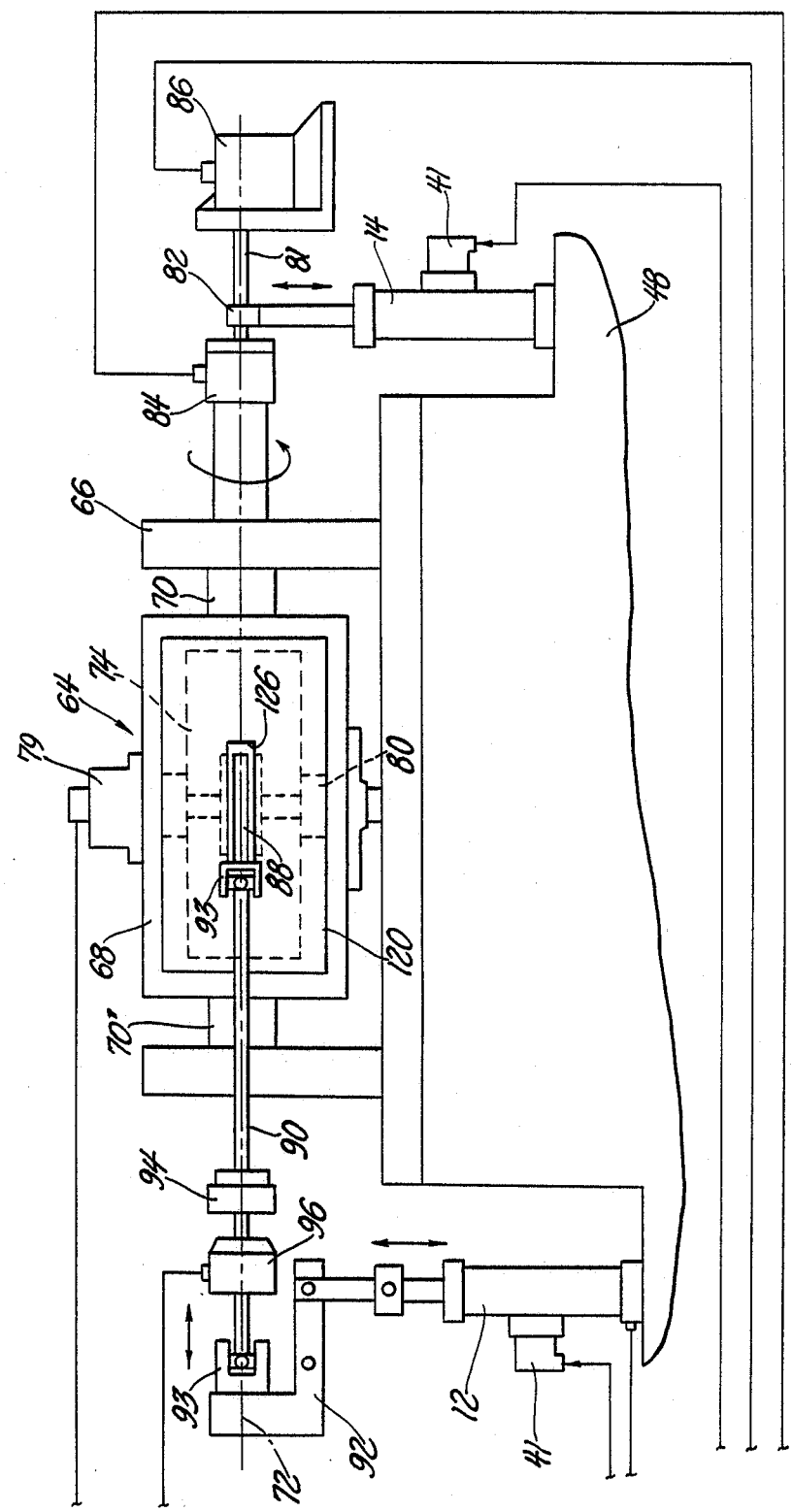
FIG. 3 is a schematic side view of the testing machine according to the invention.
Figure 4:
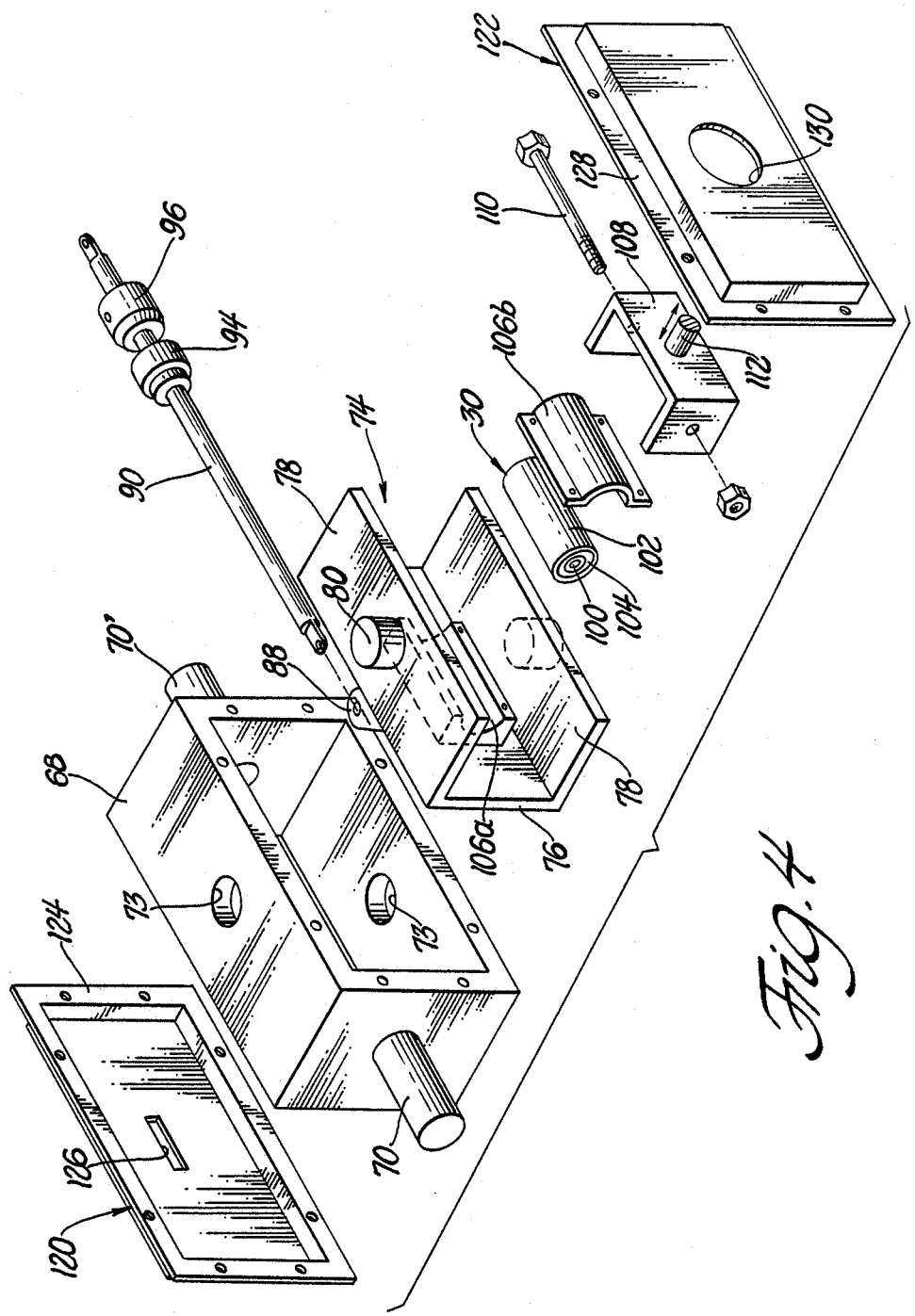
FIG. 4 is an exploded view of the gimbal assembly of the machine of FIGS. 2 and 3.

FIGS. 2, 3 and 4 reveal the hardware of the testing machine. The machine has a base 48 which directly supports the actuators 10, 12 and 14. Each of the actuators is a linear hydraulic actuator having a hydraulic cylinder with a one-piece, double-ended rod and piston, an integral LVDT position transducer and a servovalve 41 for actuator control in response to the valve command from the actuator control.

A gimbal assembly 64 is mounted on the base 48 by a pair of spaced supports 66. The assembly 64 comprises an outer gimbal 68 having laterally extending hubs 70, 70' journaled in the supports 66 for pivotal motion about a horizontal axis 72. One of the hubs 70' is tubular thereby forming an inner passage which extends to the inside of the gimbal assembly. The outer gimbal 68 is generally rectangular and forms a four sided box. A pair of opposed apertures 73 in the top and bottom sides of the outer gimbal form journals for an inner gimbal 74 which is generally U-shaped, having a generally vertical side 76 and two horizontal sides 78 which carry hubs 80 that are pivotally mounted in the apertures 73. An RVDT 79 carried by the gimbal 68 and connected to a hub 80 generates accurate rotational position signals for the inner gimbal 74.

Actuation of the inner and outer gimbals 74 and 68 requires two actuators 12 and 14, respectively. The gimbal 68 has an extension rod 81 extending longitudinally from its hub 70 which carries a radially extending lever 82 for engagement by the rod of actuator 14 which is mounted vertically on the base 48. Short reciprocating strokes of the actuator are translated into rotary motion or oscillation of the outer gimbal. A torque cell 84 between the lever 82 and the hub 70 develops torque feedback signals. An RVDT 86 on the extension 81 generates accurate rotational position signals for the outer gimbal. The inner gimbal 74 has a lever 88 extending outwardly from the side plate 76 which is pivotally coupled to one end of a push rod 90. The other end of the push rod 90 is pivotally mounted to a bell crank 92 which in turn is connected to the actuator 12 which is also vertically mounted on the base 48. To assure that only forces in the longitudinal direction of the push rod 90 are transmitted to the lever 88 the pivot action at each end of the push rod is afforded by universal joints 93, and a rotary coupling 94 is provided intermediate the push rod ends. A load cell 96 is also inserted in the push rod to provide force measurements.

An important aspect of the linkage geometry is that the pivot point of the push rod 90 and the crank 92 is on the axis 72 of the outer gimbal 68. This allows the actuation of the inner gimbal without parasitic motion of the outer gimbal. In other words cross talk is avoided so that the inner gimbal is simultaneously rocked about two axes and each motion is independent of the other. Each gimbal is affected only by the programmed force or displacement for that gimbal so that specified test conditions can be maintained. The arcuate movement of the end of the bell crank introduces only a small deviation of the pivot point from the axis 72. For greater accuracy the actuator 12 can be aligned with the axis 72 and the bell crank eliminated but that arrangement is less compact than the preferred design.

The test specimen or bushing 30 has an inner sleeve 100, an outer sleeve 102 and an elastomer spacer 104. A two-part clamp 106a, 106b secures the outer sleeve 102 to the inner wall of the inner gimbal 74 such that the outer sleeve 102 is coaxial with the hub 70 of the outer gimbal 68 when no input force is applied. A bifurcated yoke 108 is clamped to the ends of the inner sleeve 100 by a bolt 110 which passes through the sleeve 100. The yoke 108, in turn is attached to a shaft 112 which is connected to the actuator 10 through an insulator 114 and a load cell 116. The load cell 116 provides a load signal to the control 18. The insulator 114 maintains the yoke and the inner sleeve 100 isolated from ground potential so long as the elastomer spacer 104 is intact. Upon failure of the elastomer the inner and outer sleeves contact to ground the yoke 108. The failure sensor 36 is an electrical contact in circuit with the yoke 108 for sensing the potential of the yoke 108 thereby providing a failure indication when ground potential is detected. Alternative failure indications are changes in the displacement for a given input force or changes in force for a given displacement.

For the purpose of maintaining the bushing at a desired test temperature a chamber 118 enclosing the bushing is formed by the outer gimbal 68 and a pair of sheet metal covers 120 and 122. Cover 120 has a flange 124 for attachment to the rear side of the gimbal 68 and a central aperture 126 for admitting the lever 88 of the inner gimbal 74. The cover 122 also has a flange 128 for attachment to the front of the gimbal 68 and an aperture 130 to admit the shaft 112. The apertures 126 and 130 also provide vents for the escape of air from the chamber which allows heated air to be blown into the chamber. A blower 132 outside the chamber 118 is coupled via a duct 138 to the tubular hub 70' of the gimbal 68 to force air into the chamber 118 and an electrical resistance heater 136 in the air passage heats the air to a controlled temperature. The thermocouple 32 in the chamber 118 transmits a temperature signal to the temperature control 24 which controls the heater 136. With this arrangement the temperature of the chamber can be held to within about one degree C of a set value in the range of 50° to 120 degrees C.

A particular testing machine is designed with flexibility to test bushings of various sizes under various selected input forces or displacements. For example, one such machine has an actuator 10 having a working stroke of 10 mm, a frequency of 4 Hz and a maximum working load of + or −24 KN, an actuator 12 having a working stroke of 22.6 mm, a frequency of 4 Hz and produces a maximum rotation of the inner gimbal 74 of + or −15 degrees and a maximum torque of 400 in-lbs, and an actuator 14 having a working stroke of + or −32 mm, a frequency of 5 Hz, and produces a maximum rotation of the outer gimbal 68 of + or −30 degrees and a maximum torque of 2000 in-lbs. within these ranges, the machine is set to test a given bushing design in a manner to simulate real usage conditions. For example, a certain bushing having a length of 59 mm, an outer diameter of 47 mm and an inner diameter of 14 mm is tested at a 6000N radial load applied by the actuator 10, a displacement of + or −30 degrees of the outer gimbal at a frequency of 3 Hz, and a displacement of + or −1 degree of the inner gimbal at a frequency of 1 Hz. Bushings of different sizes are accommodated by substitution of appropriately sized clamps 106a, 106b and yoke 108.

It will thus be seen that the testing machine according to the invention provides flexibility of test conditions about three axes, and accurate measurement and control of the loads and displacements as well as temperature control.

The embodiments of the invention in which an exclusive property or privilege is claimed are defined as follows:

1. A testing machine for multi-axis fatigue testing of a component having inner and outer elements subject to linear and rotational forces about different axes comprising
a base,
first, second and third hydraulic actuators secured to the base,
hydraulic pressure means and control means coupled to the actuators for controlled operation of the actuators,
gimbal means comprising first and second gimbals mounted on the base and interconnected for rotation about mutually perpendicular axes, the first gimbal having means for attachment to one of the elements,
means for substantially independently coupling the first and second actuators to the first and second gimbals respectively so that each actuator effects rocking movement of one gimbal without inputting torque about the axis of the other gimbal, and
means for attaching the third actuator to the other of the elements, whereby the three actuators independently and controllably apply loads to the component about three axes of motion.

2. The machine as defined in claim 1 wherein the third actuator is a linear actuator directly coupled to the component to apply a linear load.

3. The machine as defined in claim 2 wherein the first gimbal is clamped to the outer element to hold the component on the axis of the second gimbal, and the third actuator is attached to the component by a yoke clamped to the inner element.

4. The machine as defined in claim 2 wherein the first and second actuators are linear actuators and the means for coupling the first and second actuators to the gimbals include crank means for effecting rocking motion of the gimbals.

5. The machine as defined in claim 4 wherein the crank means for coupling the first actuator to the first gimbal comprises a crank which is connected to the first gimbal by a link pivotally connected to the crank and the pivot point of the link and the crank is substantially on the axis of the second gimbal.

6. The machine as defined in claim 1 including a chamber for enclosing the component, the gimbal means defining at least part of the chamber, and the testing machine further includes means for supplying heat to the chamber to heat the component to test temperature.

7. The machine as defined in claim 6 wherein the means for supplying heat to the chamber includes a tubular pivot member forming a support for the gimbal means and means for introducing heated air into the chamber through the tubular pivot member.

8. The machine as defined in claim 1 including a stationary gimbal support mounted on the base and wherein the second gimbal includes a hollow hub rotatably mounted on the support and forming an air passage, the gimbal means forming a test chamber connecting to the air passage and containing the component, means for heating air, and means for blowing the heated air through the air passage in the hub for heating the test chamber.

9. The machine as defined in claim 8 including apertured cover means wherein the test chamber formed by the gimbal means is bounded by the cover means and the second gimbal, the cover apertures allowing attachment of the first and third actuators to the gimbal means and the component respectively as well as the escape of air from the chamber.

* * * * *